United States Patent
Simi et al.

(10) Patent No.: US 12,059,226 B2
(45) Date of Patent: Aug. 13, 2024

(54) MASTER CONTROLLER ASSEMBLY FOR A ROBOTIC SURGERY SYSTEM AND METHOD

(71) Applicant: MEDICAL MICROINSTRUMENTS, INC., Wilmington, DE (US)

(72) Inventors: Massimiliano Simi, Pisa (IT); Giuseppe Maria Prisco, Pisa (IT)

(73) Assignee: MEDICAL MICROINSTRUMENTS, INC., Wilmington, DE (US)

( * ) Notice: Subject to any disclaimer, the term of this patent is extended or adjusted under 35 U.S.C. 154(b) by 867 days.

(21) Appl. No.: 17/056,375

(22) PCT Filed: May 17, 2019

(86) PCT No.: PCT/IB2019/054097
§ 371 (c)(1),
(2) Date: Nov. 17, 2020

(87) PCT Pub. No.: WO2019/220408
PCT Pub. Date: Nov. 21, 2019

(65) Prior Publication Data
US 2021/0196417 A1    Jul. 1, 2021

(30) Foreign Application Priority Data
May 17, 2018   (IT) .................... 102018000005468

(51) Int. Cl.
*A61B 34/00* (2016.01)
*A61B 34/37* (2016.01)
(Continued)

(52) U.S. Cl.
CPC .............. *A61B 34/74* (2016.02); *A61B 34/37* (2016.02); *A61B 2017/00221* (2013.01);
(Continued)

(58) Field of Classification Search
CPC ......... A61B 34/74; A61B 34/37; A61B 90/60; A61B 2017/00221; A61B 2017/00862;
(Continued)

(56) References Cited

U.S. PATENT DOCUMENTS

| | | |
|---|---|---|
| 5,634,918 A | 6/1997 | Richards |
| 5,876,325 A | 3/1999 | Mizuno et al. |

(Continued)

FOREIGN PATENT DOCUMENTS

| | | |
|---|---|---|
| WO | 2012064361 A1 | 5/2012 |
| WO | 2014151621 A1 | 9/2014 |

(Continued)

OTHER PUBLICATIONS

International Search Report and Written Opinion of the International Searching Authority for International Patent Application No. PCT/IB2019/054097 mailed Jul. 4, 2019, 13 pages.

*Primary Examiner* — Eugene T Wu
(74) *Attorney, Agent, or Firm* — Merchant & Gould P.C.

(57) ABSTRACT

A master controller assembly for a robotic surgery system has a slave robot assembly having a slave surgical grip device providing a grip degree-of-freedom of motion lying in a predefined slave grip plane and a control unit. The master controller assembly has a portable hand-held master input tool operatively connected to the slave robot assembly. The master input tool has a master tool body having a manipulandum surface, to be hand-held by the surgeon's fingers. The master input tool is mechanically unconstrained from the slave robot assembly and has a grip command detector device having an operative portion. The operative portion is manually operable by radially directed pressure action exerted at an operative surface. A sensing assembly detects the radially directed pressure action so that the radially directed pressure action exerted at the operative (Continued)

surface determines a paired slave grip motion action of the surgical slave grip device.

20 Claims, 10 Drawing Sheets

(51) Int. Cl.
  *A61B 17/00* (2006.01)
  *A61B 50/30* (2016.01)
  *A61B 90/60* (2016.01)
(52) U.S. Cl.
  CPC ............... *A61B 2017/00862* (2013.01); *A61B 2050/314* (2016.02); *A61B 90/60* (2016.02)
(58) Field of Classification Search
  CPC ........ A61B 2050/314; A61B 2034/742; A61B 2090/571; A61B 34/30; A61B 34/35; A61B 2560/0418
  See application file for complete search history.

(56) References Cited

U.S. PATENT DOCUMENTS

| | | | |
|---|---|---|---|
| 6,424,885 | B1 | 7/2002 | Niemeyer et al. |
| 6,594,552 | B1 | 7/2003 | Nowlin et al. |
| 8,996,173 | B2 | 3/2015 | Itkowitz et al. |
| 2012/0011932 | A1 | 1/2012 | Nakagawa et al. |
| 2013/0035697 | A1 | 2/2013 | Ogawa et al. |
| 2013/0321262 | A1 | 12/2013 | Schecter |
| 2015/0038981 | A1 | 2/2015 | Kilroy et al. |
| 2018/0161108 | A1* | 6/2018 | Savall ............... G06F 3/0338 |

FOREIGN PATENT DOCUMENTS

| | | |
|---|---|---|
| WO | 2016171757 A1 | 10/2016 |
| WO | 2017064303 A1 | 4/2017 |
| WO | 2017064306 A1 | 4/2017 |
| WO | 2018107062 A1 | 6/2018 |

* cited by examiner

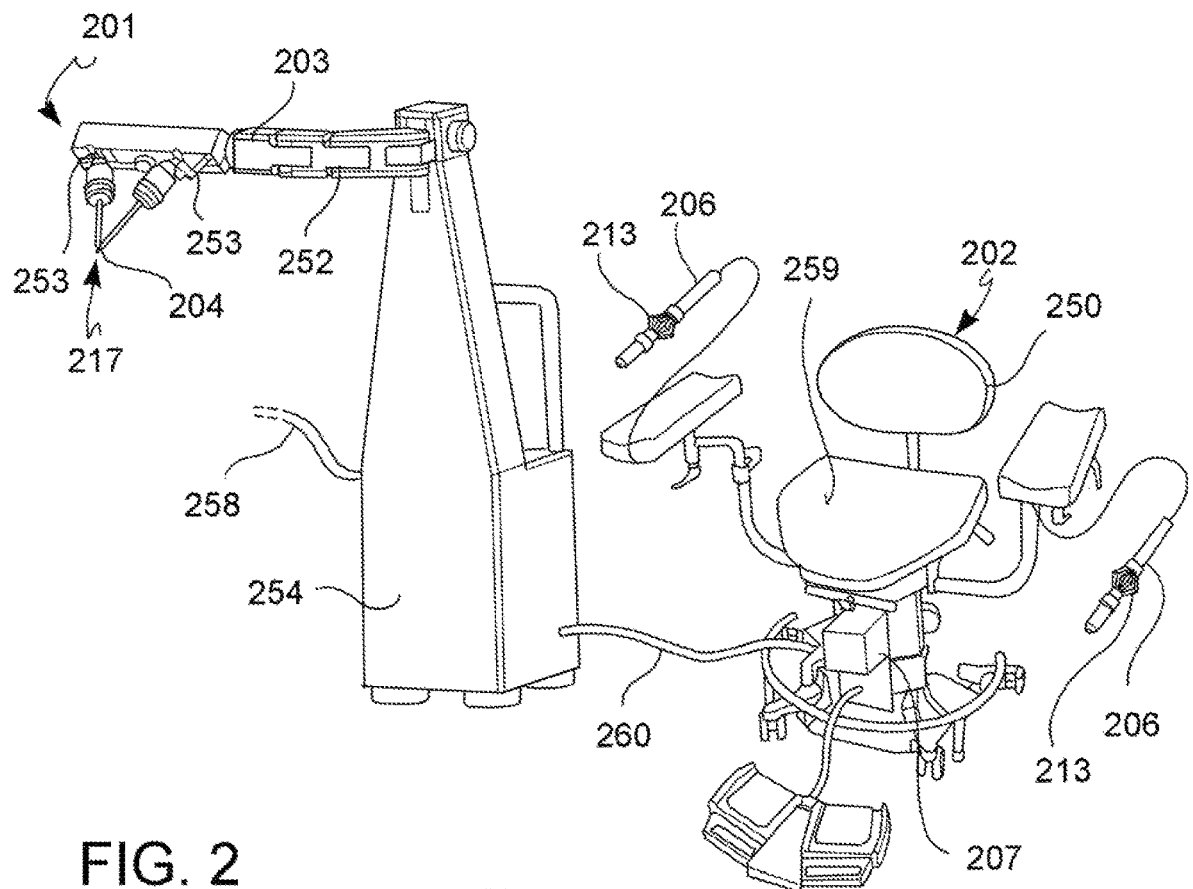
FIG. 2
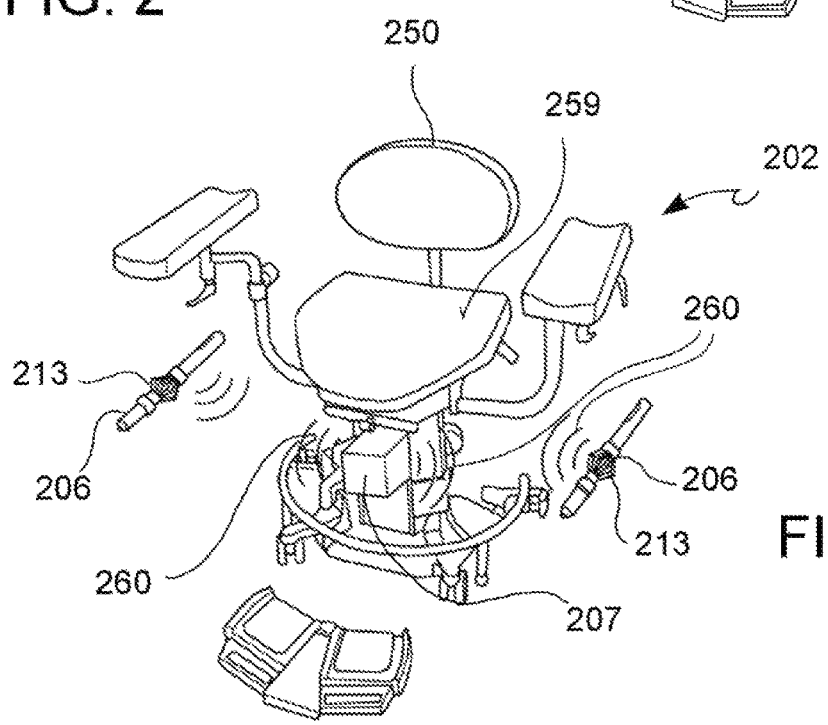
FIG. 2bis

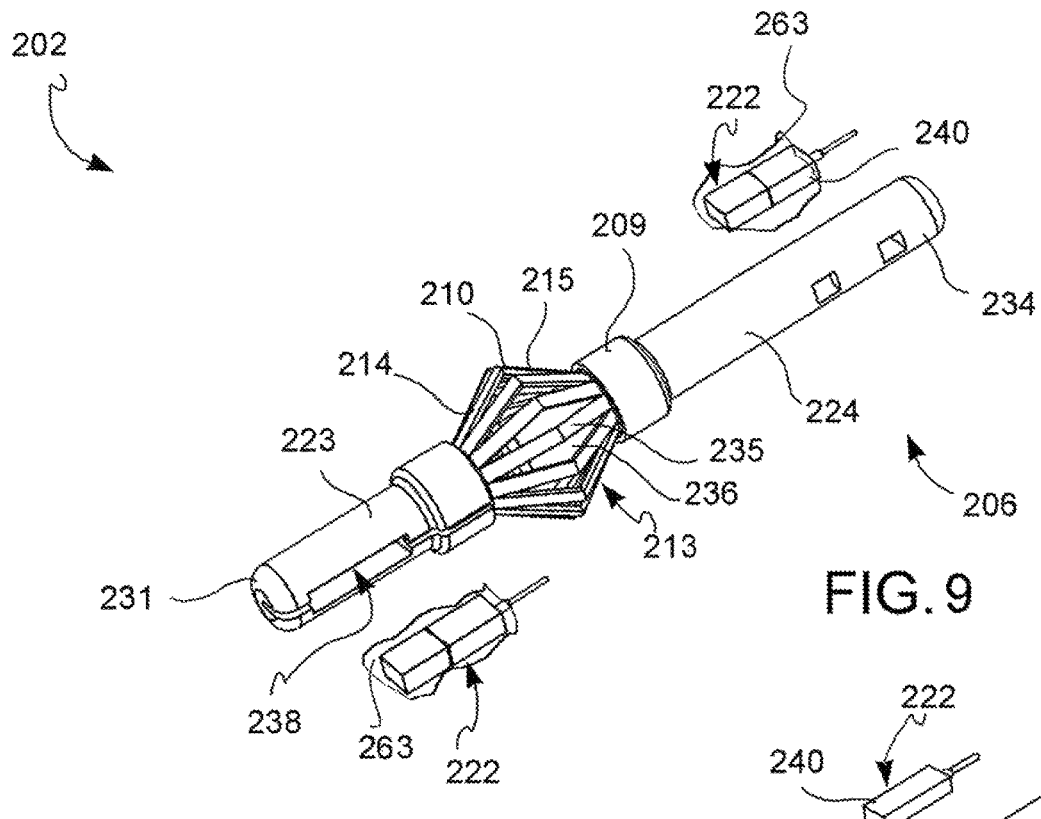
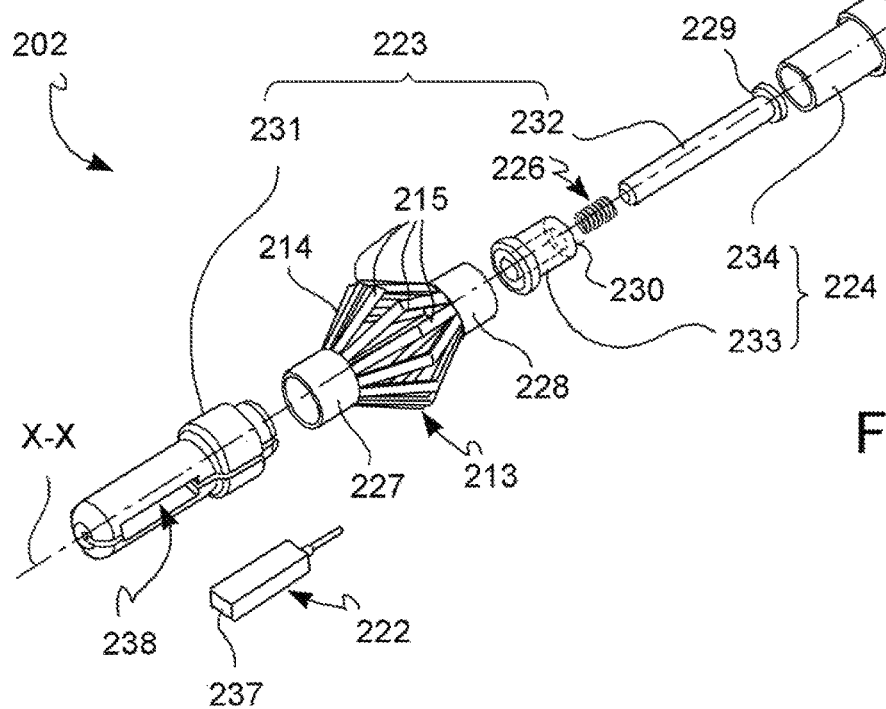

MASTER CONTROLLER ASSEMBLY FOR A ROBOTIC SURGERY SYSTEM AND METHOD

CROSS-REFERENCE TO RELATED APPLICATIONS

This application is a National Stage Application of PCT/IB2019/054097, filed 17 May 2019, which claims benefit of patent application Ser. No. 10/201,8000005468, filed 17 May 2018 in Italy and which applications are incorporated herein by reference. To the extent appropriate, a claim of priority is made to each of the above-disclosed applications.

FIELD OF THE INVENTION

It is an object of the present invention a master controller assembly for a robotic surgery system.

The present invention also relates to a robotic surgery system.

The present invention also relates to a method of controlling for a robotic surgery system.

BACKGROUND

Robotic surgical assemblies comprising a master interface and a slave surgical tool are generally known in the field. Specifically, robotic surgical assemblies of the known type comprise a master control station able to control the motion of a slave surgical end-effector, as shown for example in document U.S. Pat. No. 5,876,325. This document disclose a non-portable, robot-hung articulated appendices, which are hung to a beam fixedly constrained to the master control station, said appendices comprise master tools to control the slave surgical end-effector operating on a patient anatomy.

Similar non-portable robot-held master tool solutions are shown, for example, in documents U.S. Pat. Nos. 6,424,885 and 6,594,552, wherein the appendix of the master control station acting as master tool to control the slave surgical end-effector comprises an appendix body rigidly constrained to the master control station. The transmission of motion to the slave end-effector is based on the detection of mechanical stress induced by urging the appendix body of the master control station in various spatial directions. Such an appendix body can be associated to a pair of opposite fins, each of said fins being constrained on one of its end to the appendix body in such way to form a cantilevered fins, suitable for receiving a manual command directed to activate the grip degree-of-freedom of the slave end-effector.

However, non-portable, robot-hung or robot-held master tool solutions of the types described above exhibit some drawbacks. The provision of such control appendix mechanically constrained to the master control station of the robotic surgical assembly strongly limits the natural freedom of motion of the surgeon during surgery and forces the surgeon to operate in a predefined location from which the master control station, and particularly the control appendix attached thereto, is easily reachable. The discomfort for the surgeon is still enhanced due to the inability to real-time adjust during surgery the location, for example in terms of height from the soil, of such an appendix. That leads the surgeon to an untimely tiredness during surgery and to early focus loss.

Moreover, these known solutions have an enormous volumetric encumber within the operating room and at the same time the articulated appendix is capable of minimum range of motion. Additionally, the surgeon is forced to stay within the immersive master console, usually placed in a predetermined fixed location out the sterile region of the operating room. Further, such a master appendix is made of several mechanical parts and components assembled together, resulting in a high manufacturing time and costs.

Often, surgeons have been trained for years to properly handle surgical tools suitable for operating directly on a patient anatomy. Surgical tools are generally portable tools and comprise a tool handle, suitable to be hand-held and manipulated by the surgeon, said handle being mechanically directly connected to a tool tip, suitable for operating on a patient anatomy. Some examples of traditional ophthalmic surgery surgical tools are shown in documents U.S. Pat. No. 5,634,918 and WO-2012-064361. Such traditional surgery tools make the surgeon sure to know when the tool tip is free from touching the patient anatomy, in this way allowing the surgeon to safely (i.e. without transmitting actions on the patient anatomy) roll the tool handle between the fingers around the longitudinal axis of the tool handle, a gestural stress-reducing need rather common among surgeons for example useful for relax the hand muscles during surgery and to prevent muscular spasms. Moreover, rolling the tool handle between fingers around a longitudinal axis enables to add at least one degree of freedom of motion not driven by the surgeon wrist articulation.

Robotic microsurgery, instead, forces the surgeon to use master tools to control the motion of an associated slave end-effector operating on a patient anatomy, and usually said master tools limit the comfort of the surgeon during surgery and often force the surgeon to an additional period of training for properly using the master tool to control the slave end-effector. The additional training period can be even lengthen if the of the shape and functionalities of the master tool are alien from a traditional surgical tool.

Wearable master tool have been provided, as disclosed for example in document U.S. Pat. No. 8,996,173, wherein a pair of rings are designed to be fit on surgeon's finger and wired to the robotic slave assembly. A codified gesture set of the surgeon's finger triggers a predefined slave end-effector action on the patient anatomy. Obviously, this solution requires a very long training to the surgeon for properly managing such a wearable master rings, in order to avoid to transmit unintended commands to the slave end-effector. Unintended command transmission to the slave should be avoided for patient safety reasons.

To overcome the deficiencies of known solution described above and in order to provide an hand-held manipulandum (i.e. from the Latin: "something to be manipulated") master tool having a shape which is familiar for most surgeons, documents WO-2017-064303 and WO-2017-064306, in the name of the same Applicant, show a master tool device which substantially replicates the appearance of a traditional surgery tweezers. Such master tool device comprises a pair of flexible strips of metal welded together in one of their ends to form a tweezers-like master input device. Suitably located sensors help the magnetic pad to track the motion of the tweezers and detect when the tweezers close and to transmit the detected motion to the slave surgical end-effector.

Although satisfactory to improve the surgeon's comfort during surgery, this type of solution is prone to drawbacks. In particular, such flexible metal strips forming a tweezers-like device force a non-linear motion of the sensors placed on the free end of the metal strips, thus the detection of the manually-induced tweezers closing motion, for mimicking a sort of object grasp, often leads to measurement uncertainty and low sensing resolution. Mechanical vibrations arising in each metal strip during its elastic bending generate noise detected by the tracking pad. That could result in an unsatisfactory motion response of the slave end-effector that could even lead to serious complications in the patient body after surgery. Moreover, the tracking pad is suitable for generating a tracking magnetic field only from one side of the pad, forcing the surgeon not to move the manipulandum hand-held master tool on the back side of the pad, where the motion cannot be tracked, thus a command signal cannot be transmitted to the end-effector.

Furthermore, documents WO-2014-151621 and US-2015-038981 disclose a portable, hand-held master input tool manipulatable by a surgeon while moving in various locations of the operating arena. This solution exploits video-camera tracking of suitably designed balls that protrudes cantilevered from the portable hand-held master tool body. In other words, a set of three non-symmetric balls mounted on the master tool can be tracked by a camera apparatus provided on-robot to determine the position and orientation of the master input tool with the aim to transmit a command signal to the slave surgical end-effector. Other examples of portable, hand-held controllers are disclosed by documents WO-2018-107062 and WO-2016-171757. These solutions both comprise a inner annular chamber inside the body of the controller hosting a motor to provide tactile feedback to the user.

Although satisfactory under some points of view, these solutions are prone to drawbacks. As the visual-cues-based tracking system allows the surgeon to operate while moving in various locations of the operating arena, at the same time force the robot to have a powerful control system and can result in an unwanted delay of transmission of motion to the slave end-effector, resulting in a discomfort for the surgeon. Moreover, this solution fails to replicate the shape of a traditional surgery tool, resulting unfamiliar for the surgeon, forcing surgeons to lengthen dedicate training periods.

The need is felt to provide a master input tool solution for robotic surgery able to overcome the drawbacks cited with reference to the prior art.

The need is felt to provide a master input tool for robotic surgery suitable for improving the surgeon's comfort and at the same time able to provide a high sensing accuracy.

The need is felt to provide a master input tool for robotic surgery able to reduce to a minimum the length of the surgeon training.

The need is felt to provide a hand-held master input tool for robotic surgery being manipulatable with finger's mobility avoiding the need to being moved by the surgeon's wrist.

The need is felt to provide a hand-held master input tool for robotic surgery being sterile, allowing the surgeon to operate besides a patient anatomy.

The need is felt to provide a master input tool for robotic surgery suitable for avoiding the transmission of unwanted command signal to the slave end-effector.

The need is felt to provide a master input tool for robotic surgery devoid of mechanical constraint to the master control station or to the slave robot.

SUMMARY OF THE INVENTION

It is a scope of the present invention to overcome the drawbacks mentioned with reference to the prior art.

These and other scopes are achieved by a master controller assembly, a robotic surgery system and a method for controlling a slave grip degree of freedom in a robotic surgery system.

Some preferred embodiments are also described.

According to an aspect of the invention, a master controller assembly for a robotic surgery system comprises at least a portable hand-held master input tool and at least one sensing assembly. The master input tool comprises a master tool body defining a tool longitudinal axis, and a grip command detector device. Said master tool body comprises a at least one manipulandum surface, designed to be hand-held by the surgeon's fingers, is a convex surface, so that said master tool body can be rolled between surgeon's fingers around the tool longitudinal axis. Said master input tool is mechanically unconstrained from said slave robot assembly, in such way that said master tool body being naturally movable, rotatable and spinnable by a surgeon.

The grip command detector device of the master input tool detects said manual command, said manual command being directed to actuate the grip degree-of-freedom of motion of said slave surgical grip device, wherein said grip command detector device comprises an operative portion surrounding the tool longitudinal axis, wherein said operative portion comprises at least one operative surface faced opposite to the tool longitudinal axis and being suitable to face the surgeon's fingers, and wherein said operative portion being operable by said manual command, said manual command being a radially directed pressure action exerted at any point of the operative surface.

The at least one sensing assembly of the master controller assembly detects said radially directed pressure action, in such way that said radially directed pressure action exerted at any point of said operative surface determines a paired slave grip motion action of said surgical slave grip device so that said paired grip motion of said surgical grip device lying in said predefined slave grip plane.

Thanks to the proposed solutions, the orientation of master and slave can be decoupled while transmitting a grip command action to the slave surgical instrument.

The grip command may be detected by the sensing assembly as a linear displacement of two sensors received in slots provided in the master tool body of the master assembly.

Thanks to the proposed solutions, it is provided a master controller assembly particularly suitable for robot-aided eye surgery.

BRIEF DESCRIPTION OF THE DRAWINGS

Further characteristics and advantages of the invention will appear from the description reported below of preferred embodiments, which are given as examples and are not meant to be limiting, which makes reference to the attached figures, in which:

FIGS. 1 and 2 are perspective views of robotic surgery system, according to some embodiments;

FIG. 2bis a perspective view showing master controller assembly, according to an embodiment;

FIGS. 8 and 9 are perspective views of master controller assembly wherein sensing assembly is shown as separated pieces, according to some embodiments;

FIG. 10 is a perspective exploded view of master controller assembly, according to an embodiment;

DETAILED DESCRIPTION OF PREFERRED EMBODIMENTS

Figure 1:
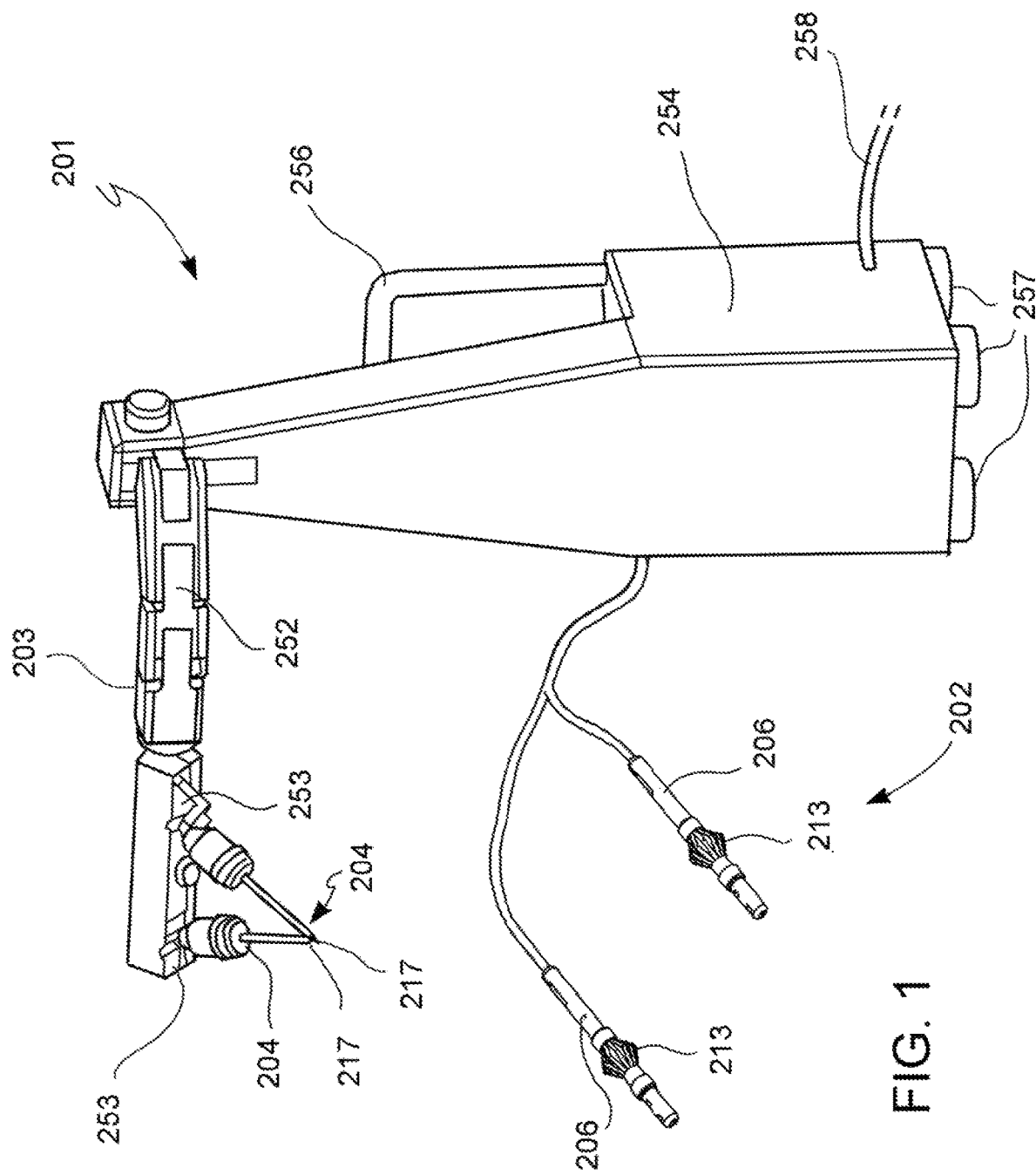
Figure 3:
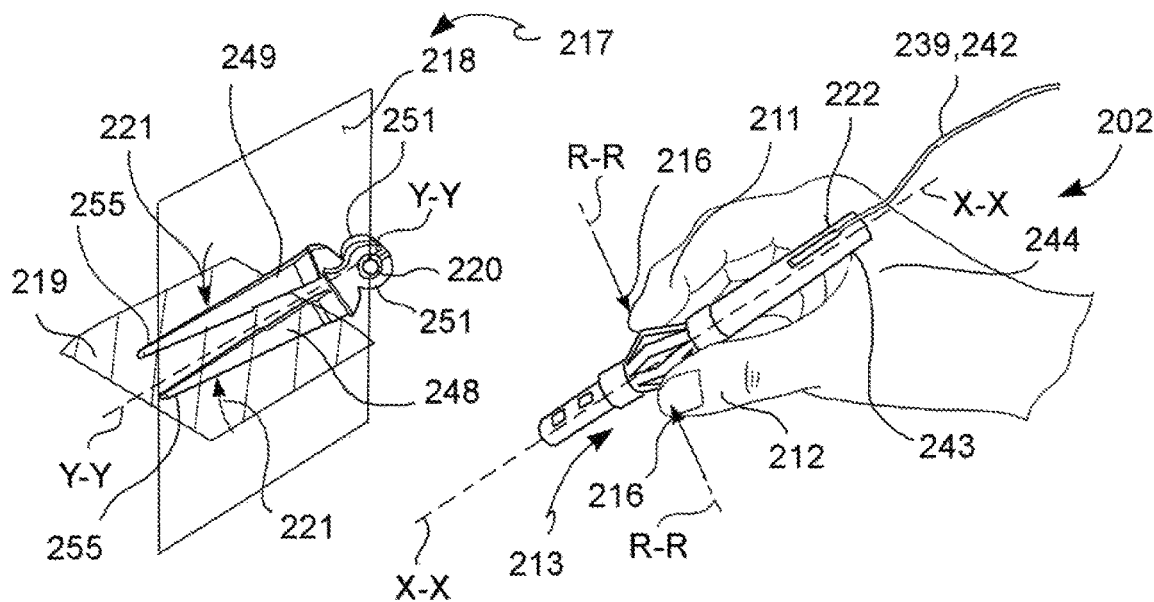
FIGS. 3 and 4 are sketches in perspective view showing master controller assembly and slave surgical grip device, according to an embodiment.
Figure 4:
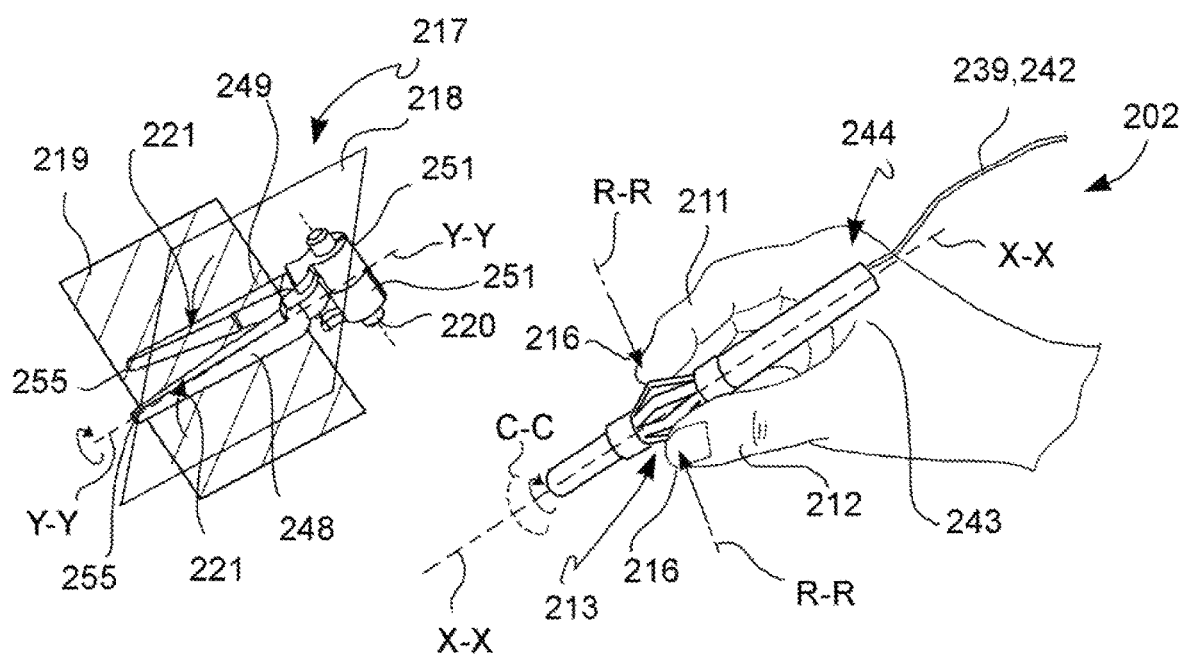
Figure 5:
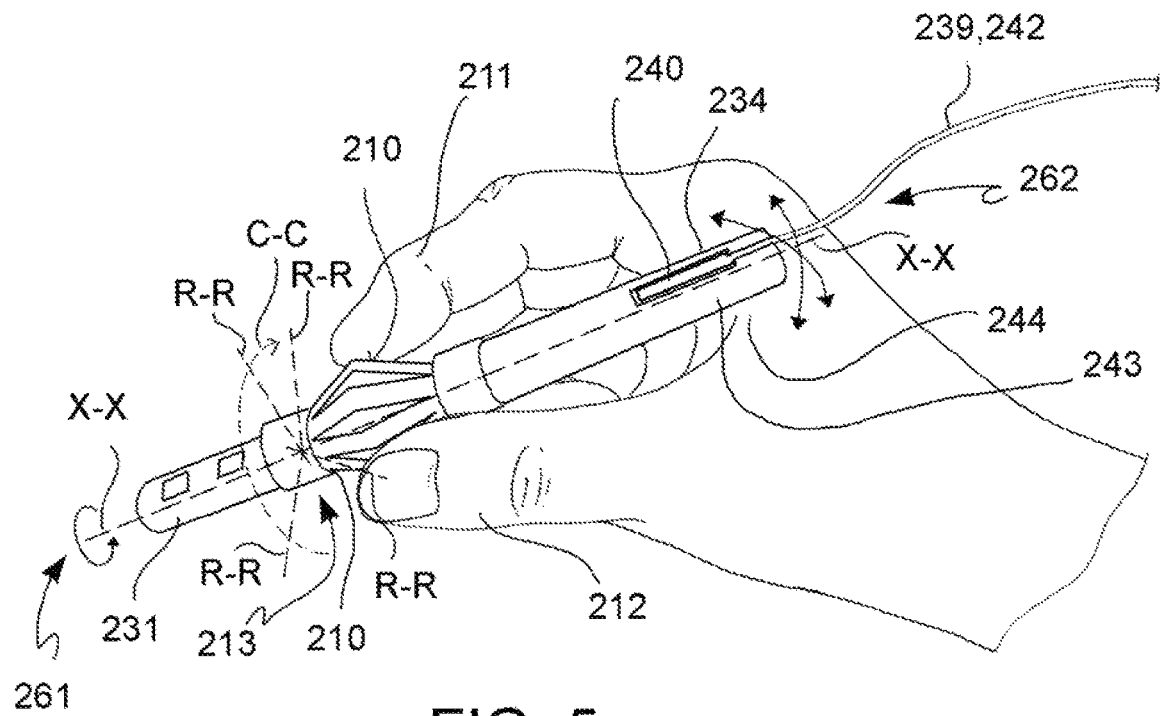
FIGS. 5, 6 and 7 are perspective views of master controller assembly hand-held by surgeon's hand, according to some embodiments.
Figure 6:
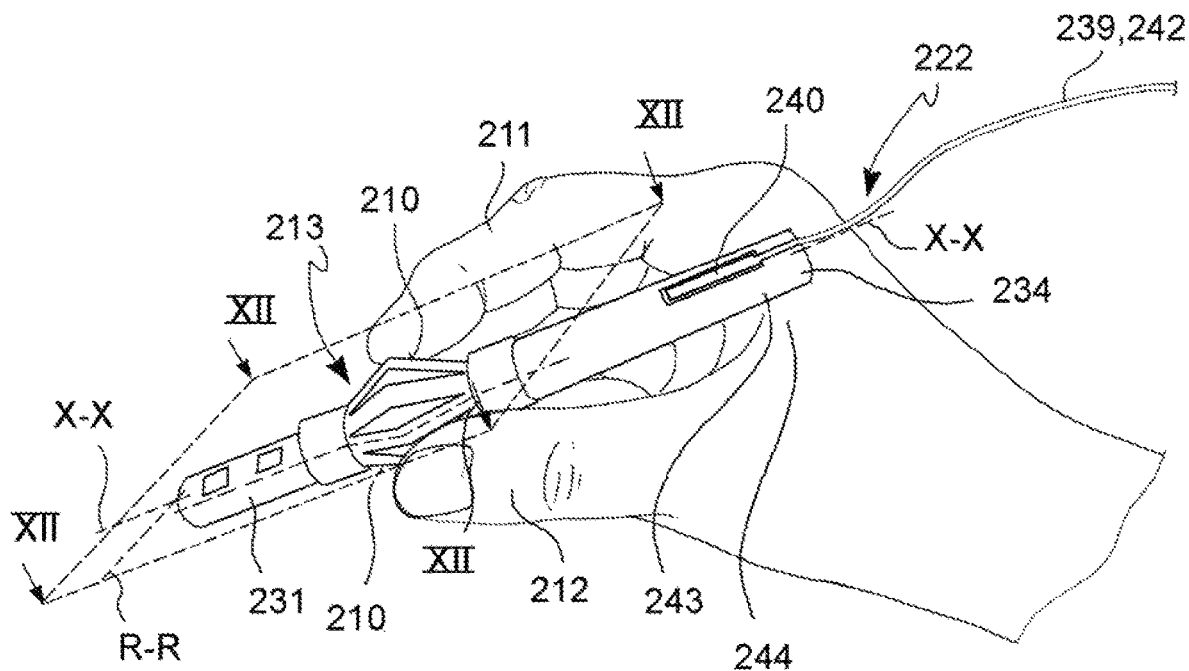
Figure 7:
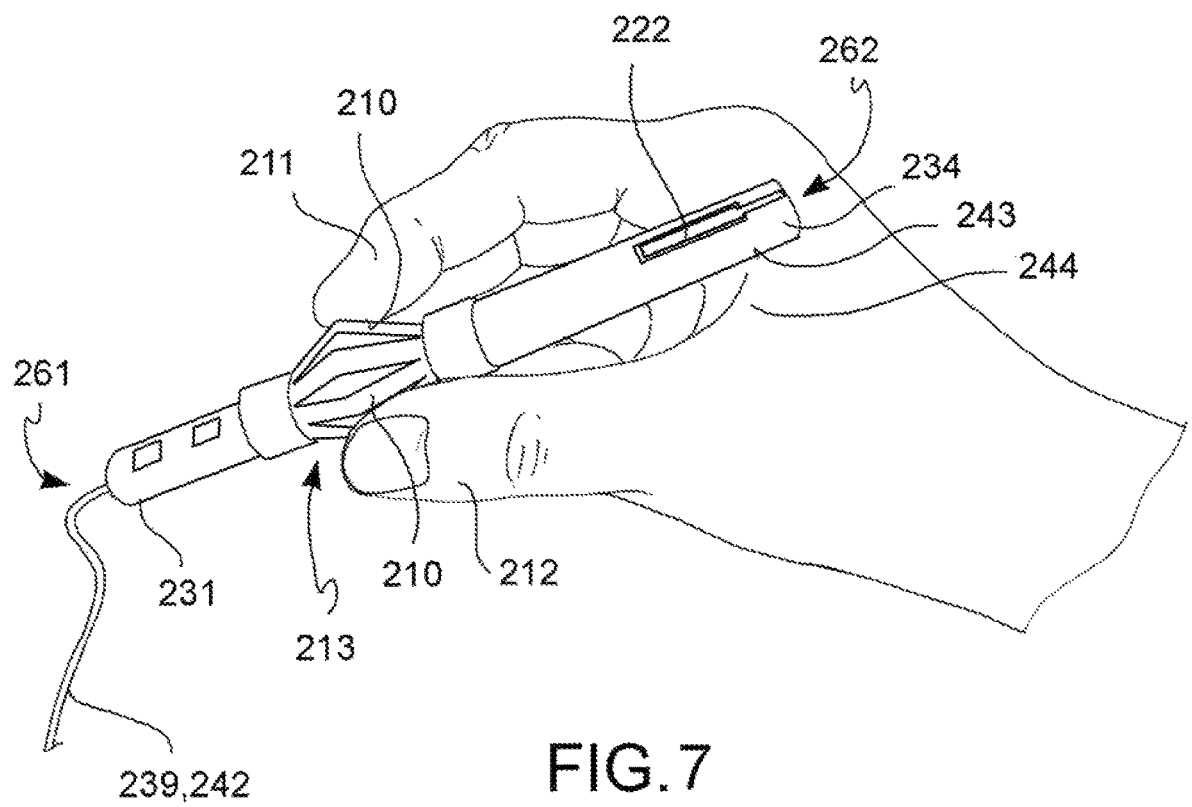
Figure 8:
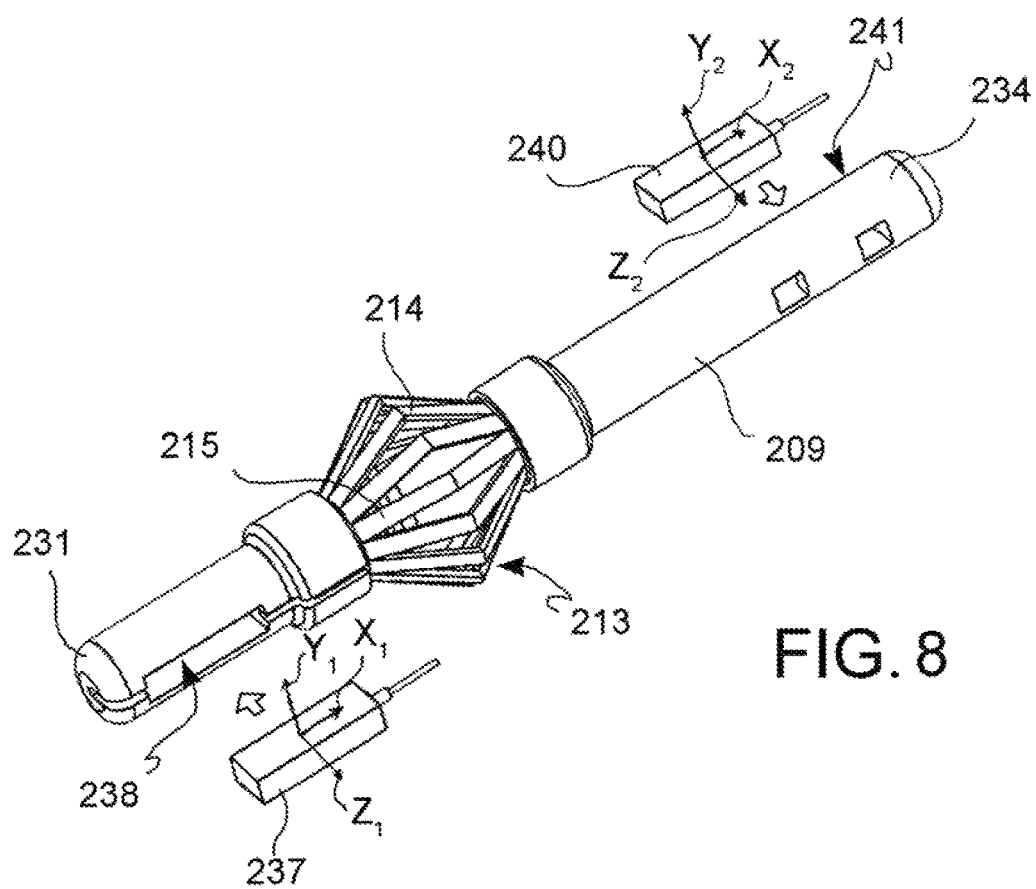
Figure 11:
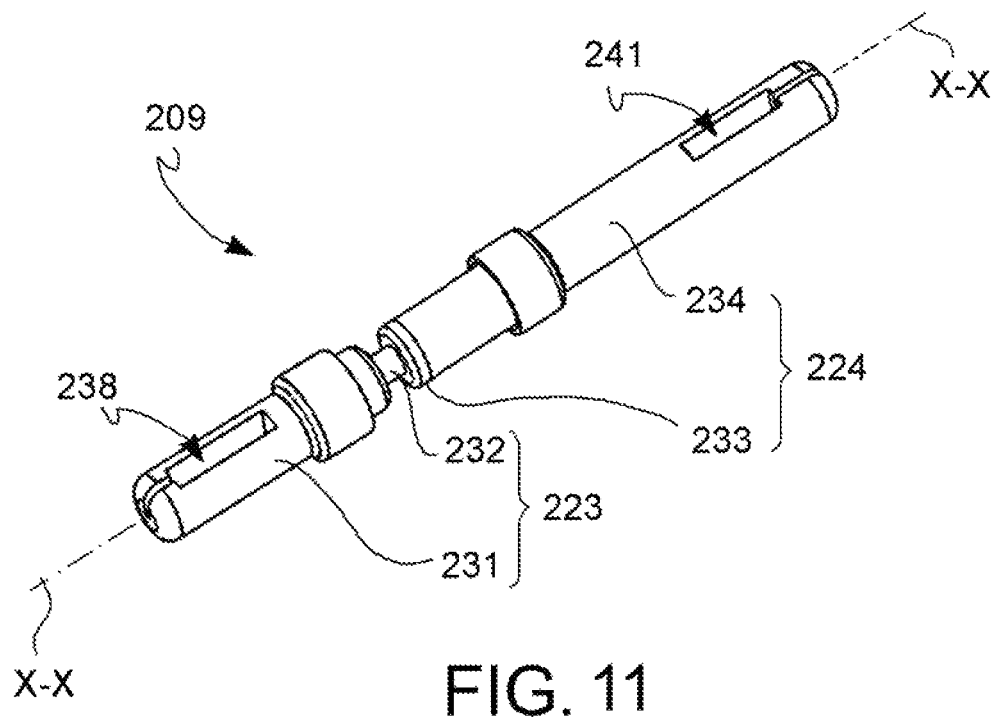
FIG. 11 is a perspective view of master tool body, according to an embodiment.
Figure 12:
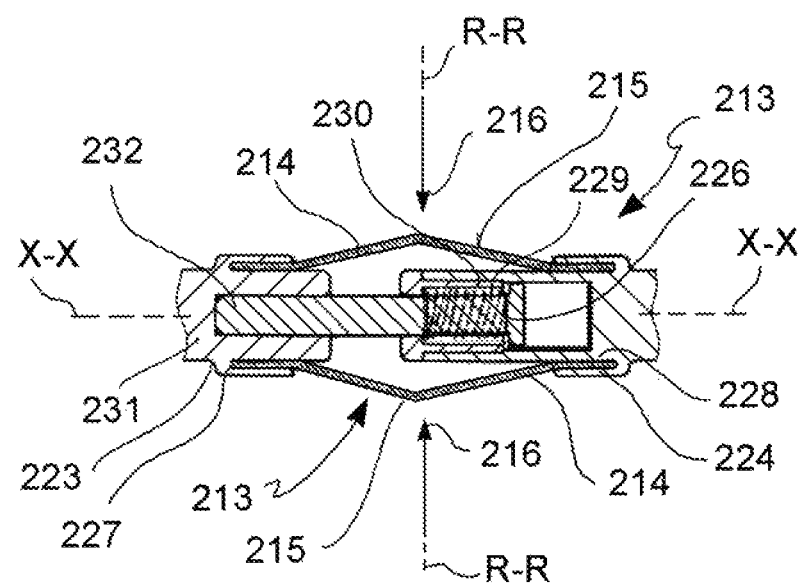
FIGS. 12, 13, 14 and 15 are cross-sections realized along a radial cutting plane as indicated by arrows XII-XII-XII-XII in FIG. 6 showing master grip command detector device.
Figure 13:
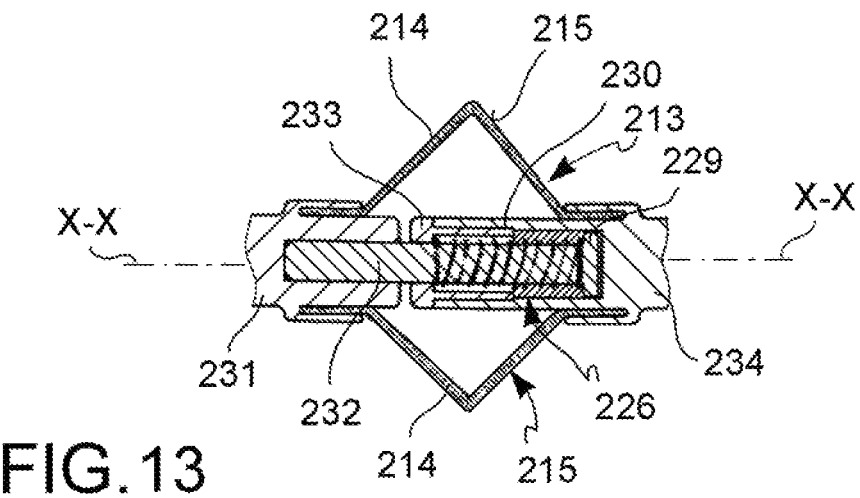
Figure 14:
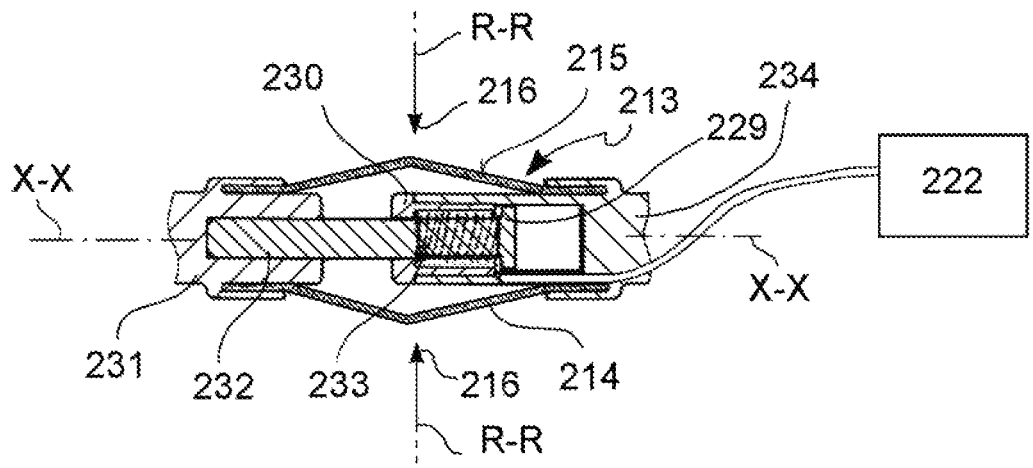
Figure 15:
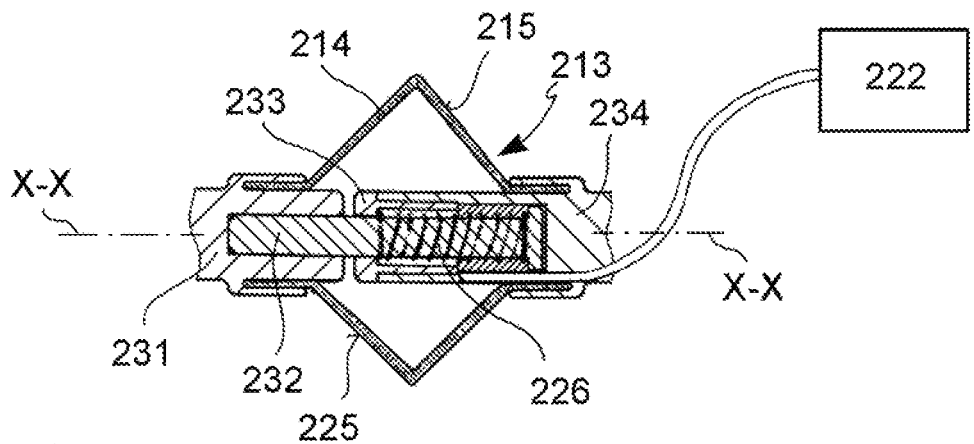
Figure 16:
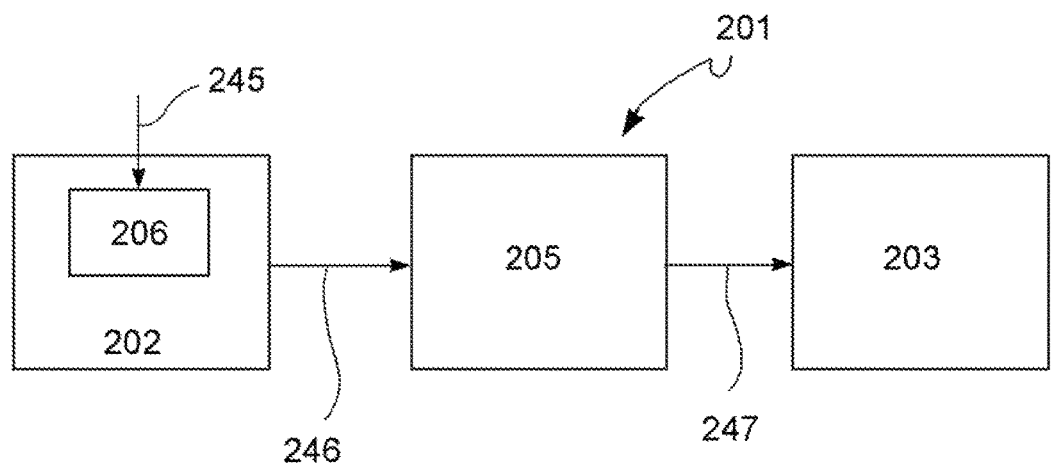
FIGS. 16 and 17 are block diagrams of a robotic surgery assembly, according to some embodiments.
Figure 17:
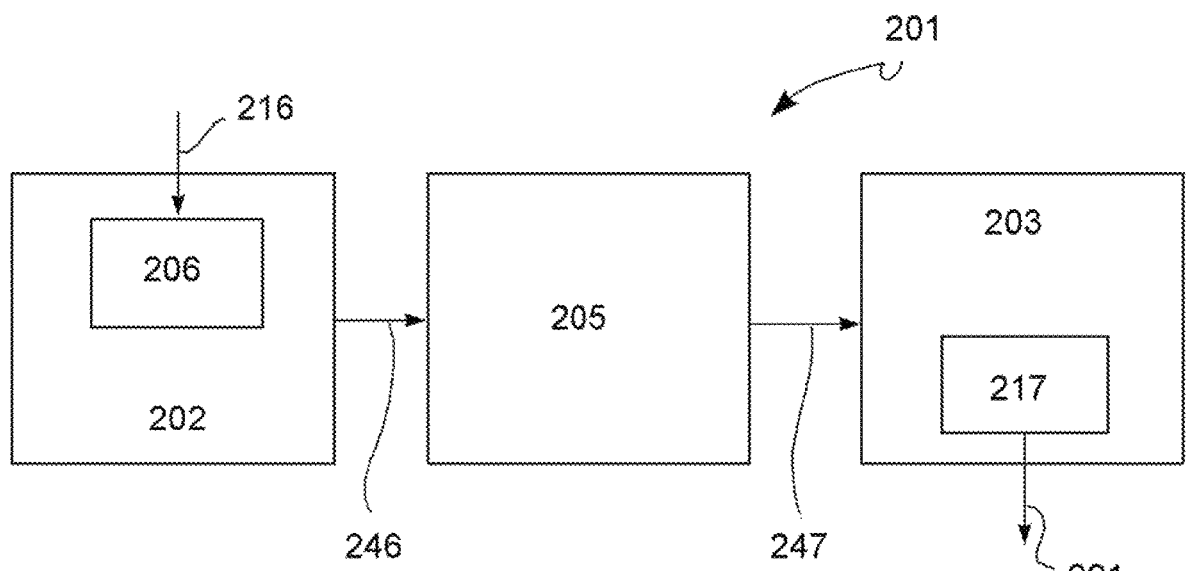
Figure 18:
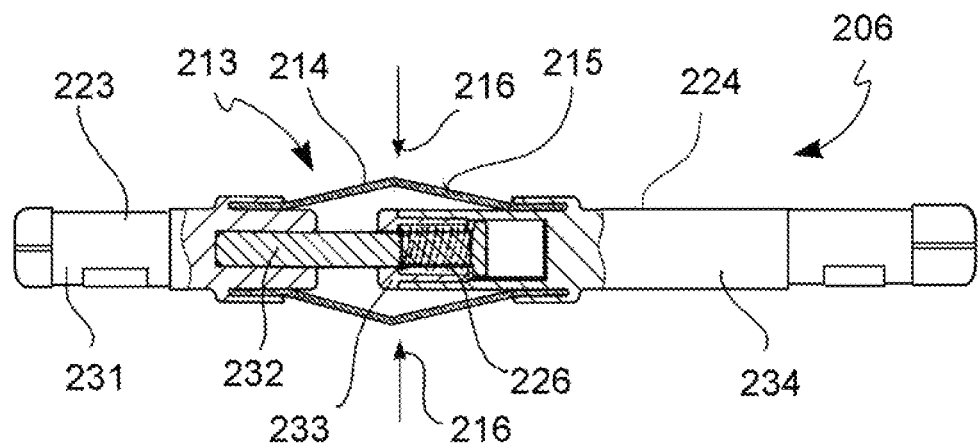
FIG. 18 is a cross-section realized along a radial cutting plane as indicated by arrows XII-XII-XII-XII in FIG. 6, showing master controller assembly, according to an embodiment, when radially directed pressure action is applied.
Figure 19:
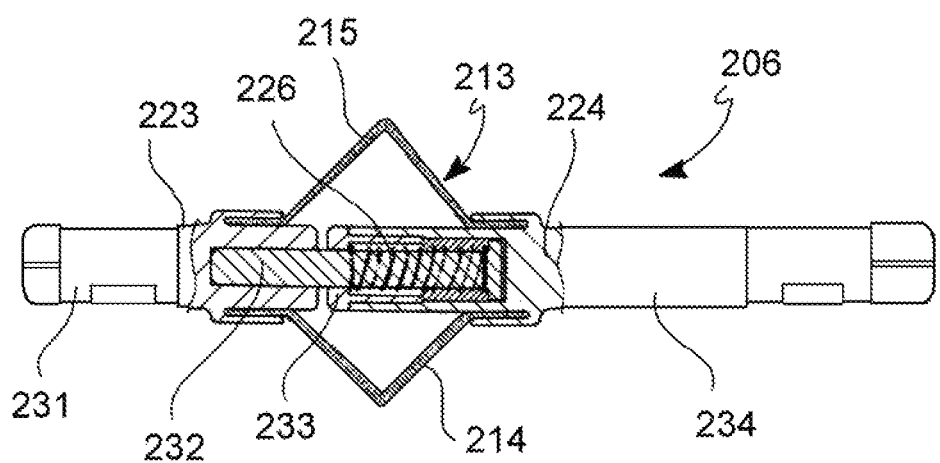
FIG. 19 is a cross-section realized along a radial cutting plane as indicated by when no manual commands are applied.

According to a general embodiment, a robotic surgery system 201 comprises at least a master controller assembly 202, suitable to detect a manual command 245, and at least one slave robot assembly 203, comprising at least one slave surgical instrument 204. Said slave surgical instrument 204 being designed to operate on a patient anatomy.

Said slave surgical instrument 204 comprises at least a slave surgical grip device 217 able to provide said surgical instrument 204 with a grip degree-of-freedom of motion lying in a predefined slave grip plane 218. According to a preferred embodiment, said slave surgical grip device 217 comprises a first elongated element 248 and a second elongated element 249, said first elongated element 248 and said second elongated element 249 being articulated in respect to one another forming a surgical grip joint 220, preferably said surgical grip joint 220 being a pin joint providing a single degree-of-freedom of motion to said first elongated element 248 and said second elongated element 249. Preferably, each of said first elongated element 248 of said slave surgical grip device 217 and said second elongated element 249 of said slave surgical grip device 217 comprises a joint portion 251, forming at least a portion of said surgical grip joint 250, and a cantilevered free end 255.

According to a preferred embodiment, said robotic surgery system 201 further comprises a control unit 205, suitable for receiving a first command signal 246 containing information about said manual command 245 and to transmit a second command signal 247 containing information about said manual command 245 to the slave robot assembly 203 in order to actuate said slave surgical instrument 204.

Said master controller assembly 202 comprises at least a portable hand-held master input tool 206, suitable to be hand-held and manipulated by a surgeon from various locations of the operating arena during surgery. In this way, said master controller assembly 202 is provided with portability, for example during surgery within said operating arena.

Said master input tool 106 being suitable for receiving said manual command 245.

According to a preferred embodiment, the term "portable" referred to said master input tool indicates that the master input tool is capable to be carried or moved about, for example by the surgeon during surgery. According to a preferred embodiment, the term "portable" referred to said master input tool indicates that the master input tool is movable in space, can be probed by hands and/or fingers, or the orientation of said longitudinal axis can be changed.

According to a preferred embodiment, the term "hand-held" referred to said master input tool indicates that the master input tool is designed to be operated while held in a hand, for example the surgeon's hand. According to an embodiment, surgeon's fingers can be used to roll or to move the master input tool while hand-held in a surgeon's hand.

According to a preferred embodiment, the term "operating arena" refers to a portion of space at least partially surrounding a patient anatomy. Preferably, within the operating arena are comprised various locations beside the patient anatomy.

According to a preferred embodiment, the term "manipulated" referred to said master input tool indicates that the master input tool can be treated or operated with or as if with hands.

According to a preferred embodiment, said master input tool 206 is paired along a master-slave pair to said slave surgical instrument 204. According to a preferred embodiment, said master input tool 206 and said slave surgical instrument 204 form, trough said control unit 205, a master-slave pair.

Said master controller assembly 202 is operatively connected to said slave robot assembly 203.

Said master input tool 206 comprises a master tool body 209. Preferably, said master input tool body 209 defines the volumetric encumber of said master input tool 206.

Said master tool body 209 defines a tool longitudinal axis X-X, coincident to the axis of longitudinal development of said master tool body 209, a tool radial direction R-R, orthogonal to the tool longitudinal axis X-X, and a tool circumferential direction C-C, orthogonal to both the tool longitudinal axis X-X and the tool radial direction R-R.

Said master tool body 209 comprises at least one manipulandum surface 210, designed to be hand-held by the surgeon's fingers 211, 212. In this way, the portability of the master input tool 206 is enhanced.

Said master input tool 206 is mechanically unconstrained from said slave robot assembly 203, in such way that said master tool body 209 is, preferably naturally, movable, rotatable and spinnable by a surgeon. According to an embodiment, said master input tool is unsuitable for providing force feedback. Said master input tool 206 is mechanically ungrounded. The master controller assembly 202 is also mechanically unconstrained and ungrounded.

Said at least one manipulandum surface 210 is a convex surface, so that said master tool body 209 can be rolled between surgeon's fingers 211, 212 around the tool longitudinal axis X-X.

According to a preferred embodiment, said master input tool 206 comprises a grip command detector device 213 detecting said manual command 245. Preferably, said manual command 24 being directed to actuate the grip degree-of-freedom of motion of said slave surgical grip device 217.

Said grip command detector device 213 comprises an operative portion 214 surrounding the tool longitudinal axis X-X.

Said operative portion 214 comprises at least one operative surface 215 faced opposite to the tool longitudinal axis X-X and being suitable to face the surgeon's fingers 211, 212.

Said operative portion 214 being operable by said manual command 245, said manual command 245 being a radially directed pressure action 216 exerted at any point of the operative surface 214. In this way, the surgeon is allowed to manually command the slave surgical grip device 217 by pressing a radially said operative portion 214 of said master input tool 206.

Advantageously, said master input tool 206 comprises at least one sensing assembly 222 detecting said radially directed pressure action 216, in such way that said radially directed pressure action 216 exerted at any point of said operative surface 215 determines a paired slave grip motion action 221 of said surgical slave grip device 217.

With a further advantage, said paired slave grip motion action 221 of said surgical grip device 217 being lying in said predefined slave grip plane 218.

Thanks to the provision of such a master input tool 206 the surgeon is allowed to command the slave surgical grip device 217 to determine said slave grip motion action 221 lying in a predefined grip plane 218 by means of applying a radially directed pressure at any point of said operative portion 214 of said master input tool 204.

The provision of such a robotic surgery system 201 makes the surgeon able to decouple or to separate the master input tool 206 orientation from the paired, along a master-slave pair, slave grip motion action 221 of the surgical grip device 217, as the paired slave grip motion action 221 lies in a grip plane 218 while the master manual command 245 can be exerted at any point of said operative surface 215, as long as being directed along said tool radial direction R-R.

Thanks to the provision of said master input tool 206, the surgeon is allowed to roll the master input tool body 209 around tool longitudinal axis X-X within surgeon's fingers 211, 212, avoiding for this reason to loss the master-slave paired operative connection with the slave surgical grip device 217.

Thanks to such a robotic surgery system 201, the surgeon commands the slave surgical grip device 217 to move of a slave surgical grip motion action 221 in a predefined slave grip plane 218 regardless of the orientation of the manual command 245 applied to said master grip command detector device 213, preferably onto said operative surface. Consequently, the surgeon commands the slave surgical grip device 217 regardless of the orientation of said master input tool 216.

According to an embodiment, said master input tool 206 is connected to the slave robotic assembly 203, preferably through said control unit 205, by means of at least one master wired connection 208.

According to a preferred embodiment, when said operative portion 214 is subject to said radially directed pressure action 216, the paired slave surgical grip device 217 is subject to a slave grip motion action 221 directed to move said cantilevered free end 255 of both said first elongated element 248 and said second elongated element 249 close one another.

According to a preferred embodiment, said at least one manipulandum surface 210 is located onto said operative portion 214 of said master grip command detector device 213. In other words, said operative portion comprises said at least one manipulandum surface 210.

According to a preferred embodiment, said operative surface 215 of said master grip command detector device 213 comprises said at least one manipulandum surface 210. In other words, said operative surface 215 comprises said at least one manipulandum surface 210.

The provision of such a manipulandum surface 210 allows the surgeon to naturally hand-holding the master input tool 206, as well to naturally manipulating the master input tool 206, for example rolling the master input tool around tool longitudinal axis X-X, and at the same time allows the surgeon to command the slave grip degree-of-freedom of the slave surgical instrument 204 of said robotic surgery system 201.

According to an embodiment, said operative portion 214 of said master grip command detector device 213 completely surrounds said tool longitudinal axis X-X. In this way, the extent of said operative surface can be maximized.

According to a preferred embodiment, said at least one manipulandum surface 210 is at least a portion of a cylindrical surface.

According to an embodiment, said operative portion 214 surrounding a prevailing angular portion of said tool longitudinal axis X-X. Preferably, said prevailing angular portion covers along the circumferential direction C-C an angle greater than 180 degrees, preferably greater than 240 degrees. According to a preferred embodiment, said prevailing angular portion covers along the circumferential direction C-C an angle greater than 270 degrees.

According to an embodiment, said operative surface 215 is a discontinuous surface, preferably formed by a plurality of disjoined surface portions all lying onto a virtual geometrical surface surrounding at least partially said tool longitudinal axis X-X.

According to an embodiment, said operative portion 214 comprises a plurality of strip elements 235 arranged substantially oriented in the tool longitudinal radial direction X-X, said plurality of strip elements 235 extending longitudinally between said first connecting portion 227 and said second connecting portion 228 of the operative portion 214, defining longitudinal holes 236 therebetween.

According to an embodiment, said operative surface 215 is a discontinuous surface in circumferential direction C-C.

According to an embodiment, said master tool body 209 being extendable, so as to modify the volumetric encumber of said master tool 206, when in operative conditions. Preferably, said master tool body extends when said radially directed pressure action 216 is applied onto said master grip command detector device 213.

According to an embodiment, said master tool body 209 comprises a first body portion 223 and a second body portion 224, wherein said first body portion 223 and said second body portion 224 being movable in respect of each other, and wherein said grip command detector device 213 cooperates with said first body portion 223 and said second body portion 224 in such way that said radially directed pressure action 216 exerted at any point of said operative surface 215 determines the relative motion of said first body portion 223 and said second body portion 224 along a predefined axis of movement, preferably said predefined axis of movement is the tool longitudinal axis X-X.

According to an embodiment, said sensing assembly 222 detects the relative motion of said first body portion 223 and said second body portion 224 along the predefined axis of movement.

According to an embodiment, said relative motion of said first body portion 223 and said second body portion 224 is directed to move said first body portion 223 and said second body portion 224 away from each other, preferably when said radially directed pressure action 216 is applied onto said master grip command detector device 213.

According to an embodiment, at least one between said first body portion 223 and said second body portion 224 comprises a guiding device 225 guiding the relative motion of said first body portion 223 and said second body portion 224.

According to an embodiment, said grip command detector device 213 of said master input tool 206 comprises an elastic element 226 biasing said operative surface 215 away from the tool longitudinal axis X-X. In this way, an elastic preload is provided on said master grip command detector device 213 that bias the operative surface 215 away from the tool longitudinal axis X-X, making said operative portion 214 ready, after having been released, to receive said manual command, preferably said radially directed pressure action 216.

According to an embodiment, said operative portion 214 comprises at least one first connecting portion 227 connected to said first body portion 223 of said master tool body 209, and at least one second connecting portion 228 connected to said second body portion 224 of said master tool body 209, in such way that said radially directed pressure action 216 exerted at any point of said operative surface 215 loads said elastic element 226.

According to an embodiment, said elastic element 226 biasing said first body portion 223 and said second body portion 224 of said master tool body 209 approaching one another.

According to an embodiment, said elastic element 226 comprises an axial spring suitable to load elastic energy when axially compressed.

According to an embodiment, said first body portion 223 comprises a first abutment portion 229, forming an abutment wall for said elastic element 226, and wherein said second body portion 224 comprises a second abutment portion 230, forming an abutment wall for said elastic element 226.

According to an embodiment, said first abutment portion 229 faces said second abutment portion 230. Preferably, said first abutment portion 229 and said second abutment portion 230 are located in an undercut manner in respect to one another, with respect to the relative movement of said first body portion and said second body portion of said master tool body 209.

According to an embodiment, said first body portion 223 comprises a distal tool body 231 and a stem element 232, said distal tool body 231 receiving a portion of said stem element 232, so that said distal tool body 231 being integral with said stem element 232. According to an embodiment, said stem element 232 comprises said first abutment portion 229.

According to an embodiment, said second body portion 224 of said master tool body 209 comprises a hollow bobbin 233 and a proximal tool body 234. According to an embodiment, said hollow bobbin 223 comprises said second abutment portion 230. Preferably, said hollow bobbin delimits a through hole directed along the tool longitudinal direction X-X.

According to a preferred embodiment, said hollow bobbin 233 is fit onto said stem element 232, in such way that said first abutment portion 229 of the stem element 232 faces said second abutment portion 230 of the hollow bobbin 230. According to an embodiment, said elastic element is fit onto said stem element 232 and interposed between said first abutment portion 229 of the stem element 232 and said second abutment portion 230 of the hollow bobbin 230.

According to a preferred embodiment, said first body portion 223 comprising said distal tool body 231 and said second body portion 224 comprising said proximal tool body 234, wherein said first body portion 223 and said second body portion 224 being movable in respect of each other, and wherein said grip command detector device 213 cooperates with said first body portion 223 and said second body portion 224 in such way that said radially directed pressure action 216 exerted at any point of said operative surface 215 determines the relative motion of said distal tool body 231 and said proximal tool boy 234 along a predefined axis of movement, preferably said predefined axis of movement is the tool longitudinal axis X-X.

According to an embodiment, said relative motion of said distal tool body 231 and said proximal tool boy 234 is directed to move said distal tool body 231 and said proximal tool boy 234 away from each other, preferably when said radially directed pressure action 216 is applied onto said master grip command detector device 213.

According to an embodiment, said elastic element 226 is suitable for exerting an elastic action when loaded by compressive axial load.

According to an embodiment, said elastic element 226 biasing said first abutment portion 229 of the stem element 232 away from said second abutment portion 230 of the hollow bobbin 230.

According to an embodiment, said robotic surgery system 201, preferably said master controller assembly 202, comprises at least one field generator 207 generating a predefined field volume. According to a preferred embodiment, said at least one filed generator 207 generates a magnetic field.

According to an embodiment, said slave robot assembly 203 further comprises at least one surgical arm 252 manipulating said slave surgical instrument 204. According to an embodiment, said salve robot assembly 203 comprises at least one micromanipulator 253 manipulating said slave surgical instrument 204. Preferably, said at least one micromanipulator 253 is directly connected in series to said surgical arm 252 forming a kinematic chain with said surgical arm 252, said micromanipulator 253 manipulating said slave surgical instrument 204. According to an embodiment, at least two micromanipulators 253 are directly connected in series to said surgical arm 252 forming an at least two-branched kinematic chain with said surgical arm 253.

According to an embodiment, said robotic surgery system 201 comprises at least one robot cart 254 comprising at least one cart ground contact unit 257 and a cart handle 256, said cart handle 256 being suitable for moving at least a portion of the robotic surgery system 201, preferably said slave robot assembly 203, at least within the operating arena. Preferably, said robot cart 254 forms a mechanical and structural support, preferably a movable mechanical and structural support, for the slave robot assembly 203.

According to an embodiment, said robot cart 254 is connected to a power supply cable 258.

According to an embodiment, said robot cart 254 comprises said control unit 205. Preferably, said control unit 205 is located integral said robot cart 254.

According to an embodiment, said robot cart 254 comprises said filed generator 207. In this way, the generated field volume is integral with said robot cart 254.

According to an embodiment, said master controller assembly 202 further comprises at least one surgical chair 250 comprising at least one seating surface 259 for the surgeon to seat thereon during surgery.

According to an embodiment, said surgical chair 250 being mechanically unconstrained from the slave robot assembly 203, so as to prevent the propagation by mechanical contact of vibrational motion from the surgical chair 250 to the slave robot assembly 203. In this way, is reduced the risk of unwanted commands transmittal to the slave surgical robot 203, and particularly to said slave surgical instrument 204.

According to an embodiment, said surgical chair 250 comprises said field generator 207 so that said field volume is integral with at least a portion of said surgical chair 250.

According to an embodiment, said master input tool 206 is operatively connected to said surgical chair 250 by means of a chair operative connection 260. According to an embodiment, said chair operative connection 260 is a wired connection. According to an embodiment, said chair operative connection 260 is a wireless connection.

According to an embodiment, said sensing assembly 222 comprises at least one capacitive incremental position sensor, for example a capacitive encoder.

According to an embodiment, said at least one sensing assembly 222 detecting at least the position, preferably at least the position and the orientation, of said master input tool 206, preferably within said predefined field volume.

According to an embodiment, said field generator 207 defines a reference zero point integral with said field generator 207, and wherein said at least one sensing assembly 222 detecting the generated field local vector X1,Y1,Z1;X2,Y2,Z2, determines at least the position of said sensing assembly 222. In this way, sensing device 222 determines at least the position, preferably at least the position and the orientation, of said master tool assembly 206 integral with said sensing device 222 within said predefined field volume.

According to an embodiment, said master input tool 206 is mechanically unconstrained from both the field generator 207 and the slave robot assembly 203, in such way that said master tool body 209 being naturally movable, rotatable and spinnable by a surgeon within said predefined field volume.

According to an embodiment, said master controller assembly 202 is operatively connected to said slave robot assembly 203 by means of electromagnetic communication.

According to an embodiment, said electromagnetic communication is a electric or electromagnetic signal communication.

According to an embodiment, said master controller assembly 202 is operatively connected to said slave robot assembly 203 by means of a wired electric connection.

According to an embodiment, said master controller assembly 202 is operatively connected to said slave robot assembly 203 by means of a wireless connection.

According to an embodiment, said sensing assembly 222 comprises at least one first sensor 237, said first sensor 237 is integral with said first body portion 223 of said master tool body 209. Preferably, said first sensor 237 being integral with said distal tool portion 231 of said first body portion 223.

According to a preferred embodiment, said first body portion 223, preferably said distal tool portion 231, delimits at least one first slot 238 receiving at least a portion of said sensing assembly 222, preferably receiving said first sensor 237. According to an embodiment, at least a portion of said sensing assembly 222, preferably said first sensor 237, is received in a detachable manner within said first slot 238, so that the master input tool 206 comprising or devoid of said sensing assembly 222 is disposable.

Preferably, said first slot 238 receives said first sensor 237.

According to an embodiment, said sensing assembly 222 comprises at least one second sensor 240. According to an embodiment, said second sensor 240 is integral with said second body portion 224 of said master tool body 209. Preferably, said second sensor 240 is integral with said proximal tool portion 234 of said second body portion 224.

According to an embodiment, said second body portion 224, preferably said proximal tool portion 234, delimits at least one second slot 241 receiving at least a portion of said sensing assembly 222, preferably said second sensor 240. According to an embodiment, at least a portion of said sensing assembly 222, preferably said second sensor 240, is received in a detachable manner within said second slot 241, so that the master input tool 206 comprising or devoid of said sensing assembly 222 is disposable.

Preferably, said second slot 241 receives said second sensor 240.

According to an embodiment, said sensing assembly 222 comprises at least one sterile sensor container 263, enclosing at least one of said first sensor 237 or said second sensor 240. In this way, sensor assembly 222 sterility is achievable without for this reason requiring sensor 237, 240 replacement. In this way, sensor assembly 222 sterility is achievable avoiding to require sensor replacement after a single surgery. For example, said sterile sensor box 263 is a plastic bag and/or a plastic box enclosing each of said sensors. Preferably, also the wired connections to sensors 237, 240 are enclosed by sterile boxes or appendix thereof.

According to an embodiment, said first slot 238 faces opposite in respect of said second slot 241, so that a unique arrangement of said sensing device 222 is allowed. In this way, the chances of misplacing sensing assembly 222 are significantly reduced. According to an embodiment, said slots 238, 241 have different flag element to each other so that a sensor 237, 240 can be operatively connected to only one of the slots 238, 241.

According to an embodiment, the arrangement of said slots 238, 241 is asymmetric. According to an embodiment, the arrangement of said sensors 237, 240 is asymmetric. According to an embodiment, said first slot 238 is opposite to said second slot 241 with respect of said tool longitudinal axis X-X.

According to an embodiment, said first body portion 223, preferably said distal tool portion 231, of said master input tool 206 defines a first longitudinal side 261. Preferably, a second longitudinal side 262 is defined opposite to said first longitudinal side 261 in respect of said master grip command detector device 213. According to an embodiment, said second body portion 224, preferably said proximal tool portion 234, defines said second longitudinal side 262.

According to an embodiment, said first sensor connection 239 and said second sensor connection 242 are both wired connections, and wherein the wires of said first sensor connection 239 and said second sensor connection 242 are both gathered on a same longitudinal side 261; 262 of said master tool body 209. In this way the encumber of said sensor connections is reduced. Preferably, said first sensor connection 239 and said second sensor connection 242 share a same wire cable unit.

According to an embodiment, said master tool body 209 comprises at least one back-of-hand resting portion 243, designed to touch at least a portion of the surgeon's back-of-hand 244, when in operative conditions.

According to a general embodiment, it is provided a master controller assembly 202 for a robotic surgery system 201 according to any one of the embodiments described above. Preferably, said robotic surgery system 201 further comprising a slave robot assembly 203 comprising a slave surgical instrument 204 having a surgical grip device able to provide said surgical instrument 204 with a grip degree-of-freedom of motion lying in a predefined slave grip plane 218.

According to a preferred embodiment, said master input tool 206 being suitable to be hand-held and manipulated by a surgeon from various locations of an operating arena during surgery; said master input tool 206 being suitable for receiving a manual command 245.

According to a preferred embodiment, said master input tool 206 comprises a master tool body 209, said master tool body 209 defines a tool longitudinal axis X-X, substantially coincident to the axis of longitudinal development of said master tool body 209, a tool radial direction R-R, orthogonal to the tool longitudinal axis X-X, and a tool circumferential direction C-C, orthogonal to both the tool longitudinal axis X-X and the tool radial direction R-R. According to a preferred embodiment, said master tool body 209 comprises at least one manipulandum surface 210, designed to be hand-held by the surgeon's fingers 211, 212.

According to a preferred embodiment, said master input tool 206 is mechanically unconstrained from said slave robot assembly 203, in such way that said master tool body 209 being naturally movable, rotatable and spinnable by a surgeon.

According to an embodiment, the terminology "mechanically unconstrained" means that no mechanical feature has a constraining effect on the free motion of portable handheld master input tool, when in operative condition. According to an embodiment, the master input tool is connected to a portion of said robotic surgery system by means of a wired connection, said wired connection being unsuitable for mechanically constraining said master input tool, when in operative conditions. The provision of such a wired connection serves to data transmittal and/or power supply, even if said wired connection can, under certain conditions, can hang the master input tool, particularly when in failure condition.

According to a preferred embodiment, said at least one manipulandum surface 210 is a convex surface, so that said master tool body 209 can be rolled between surgeon's fingers 211, 212 around the tool longitudinal axis X-X. Rolling the master input tool between surgeon's fingers around tool longitudinal axis adds at least one degree of freedom of motion to the master input tool, said additional at least one degree of freedom not being driven by the surgeon wrist articulation.

According to a preferred embodiment, said master input tool 206 comprises a grip command detector device 213 detecting said manual command, said manual command being directed to actuate the grip degree-of-freedom of motion of said slave surgical grip device 217, said grip command detector device 213 comprises an operative portion 214 surrounding the tool longitudinal axis X-X.

According to a preferred embodiment, said operative portion 214 comprises at least one operative surface 215 faced opposite to the tool longitudinal axis X-X and being suitable to face the surgeon's fingers 211, 212, said operative portion 214 being operable by said manual command, said manual command being a radially directed pressure action 216 exerted at any point of the operative surface 214.

According to a preferred embodiment, said master input tool 206 comprises at least one sensing assembly 222 detecting said radially directed pressure action 216, in such way that said radially directed pressure action 216 exerted at any point of said operative surface 215 is designed to determine a paired slave grip motion action 221 of said surgical slave grip device 217, said paired grip motion of said surgical grip device 217 being lying in said predefined slave grip plane 218.

According to an embodiment, said sensing assembly 222 comprises a plurality of parts located in various locations of the master input tool.

In the following a method of controlling a slave grip degree-of-freedom in a robotic surgery system 201 is described.

Preferably, said robotic surgery system 201 comprising at least one master controller assembly 202, suitable to detect a manual command 245, said master controller assembly 202 comprising at least one master input tool 206, and wherein said robotic surgery assembly 201 further comprising at least one slave robot assembly 203, comprising a slave surgical instrument 204, designed to operate on a patient anatomy, said slave surgical instrument 204 comprise at least a slave surgical grip device 217 able to provide a grip degree-of-freedom of motion in a predefined slave grip plane 218. Preferably, said robotic surgery assembly 201 further comprising a control unit 205, suitable for receiving information about said manual command and to transmit a command signal to the slave robot assembly 203 in order to actuate said surgical instrument 204. Preferably, said master input tool 206 comprising a master tool body 209, defining the volumetric encumber of said master input tool 206, ad wherein said master tool body 209 defines a tool longitudinal axis X-X, substantially coincident to the axis of longitudinal development of said master tool body 209, a tool radial direction R-R, orthogonal to the tool longitudinal axis X-X, and a circumferential direction, orthogonal to both the tool longitudinal axis X-X and the tool radial direction R-R.

According to an embodiment, said robotic surgery assembly 201 is as described in any one of the embodiments previously described.

According to a general operating mode, a method of controlling a slave grip degree of freedom in a robotic surgery system 201 comprises the following steps:

applying a radial directed pressure action 216 exerted at any point of an operative surface 215 of said master input tool 206;

determining a paired slave grip motion action 221 of said surgical slave grip device 217, wherein said paired grip motion of said surgical grip device 217 being lying in said predefined slave grip plane 218.

According to an operating mode, the method comprises the further step of naturally rolling the master tool body 209 between the surgeon's fingers 211, 212 around the longitudinal tool axis X-X.

According to an operating mode, the method comprises the step of repeating said steps of applying a radial directed pressure and of determining a paired slave grip motion action, preferably after having naturally rolled the master tool body 209 between the surgeon's fingers 211, 212 around the longitudinal tool axis X-X.

By virtue of the features described above, provided either separately or in combination, where applicable, in particular embodiments, it is possible to satisfy the sometimes contrasting needs disclosed above, and to obtain the aforesaid advantages, and in particular:

- it is provided a master controller assembly having familiar shape for the surgeon;
- the user command for the slave end effector to achieve grip can be applied at any point of the annular surface of the master controller, thereby decoupling the relative orientation of maser and slave;
- a magnetic tracking field is provided to detect displacement of sensors of the master controller while the surgeon actuates the annular surface to transmit the grip command.

Those skilled in art may make many changes and adaptations to the embodiments described above or may replace elements with others which are functionally equivalent in order to satisfy contingent needs without however departing from the scope of the appended claims.

LIST OF REFERENCES

201 Robotic surgery system
202 Master controller assembly
203 Slave robot assembly 204 Surgical instrument, or slave surgical instrument
205 Control unit
206 Master input tool
207 Field generator
209 Master tool body
210 Manipulaandum surface
211 Surgeon's finger
212 Further surgeon's finger
213 Grip command detector device, or master grip command detector device
214 Operative portion
215 Operative surface
216 Radially directed pressure action
217 Slave surgical grip device, or surgical grip device
218 Slave surgical grip plane
219 Grasped object
220 Slave grip joint
221 Slave grip motion action
222 Sensing assembly
223 First body portion of the master tool body
224 Second body portion of the master tool body
225 Guide device
226 Elastic element
227 First connecting portion of the grip command detector device
228 Second connecting portion of the grip command detector device
229 First abutment portion of the first body portion
230 Second abutment portion of the second body portion
231 Distal tool body portion of the first body portion
232 Stem element of the first body portion
233 Hollow bobbin of the second body portion
234 Proximal tool body portion of the second body portion
235 Strip
236 Holes
237 First sensor
238 First sensor slot
239 First sensor connection
240 Second sensor
241 Second sensor slot
242 Second sensor connection
243 Back-of the-hand resting portion of the master tool body
244 Surgeon's back-of-the-hand
245 Manual command
246 First command signal
247 Second command signal
248 First elongated element of slave surgical grip device
249 Second elongated element of slave surgical grip device
250 Surgical chair
251 Joint portion of slave surgical grip device
252 Surgical arm
253 Micromanipulator
254 Robot cart
255 Cantilevered free end
256 Cart handle
257 Cart ground contact unit
258 Power supply cable
259 Seating surface of the surgical chair
260 Chair operative connection
261 First longitudinal side
262 Second longitudinal side
263 Sterile sensor container
X-X Tool longitudinal axis
R-R Radial direction
C-C Circumferential direction
Y-Y Slave surgical instrument longitudinal axis

The invention claimed is:

1. A master controller assembly for a robotic surgery system, the robotic surgery system comprising a slave robot assembly, comprising a slave surgical instrument designed to operate on a patient anatomy, said slave surgical instrument comprising at least one slave surgical grip device operable to provide said slave surgical instrument with a grip degree-of-freedom of motion lying in a predefined slave grip plane and a control unit, for receiving a first command signal containing information about a manual command and for transmitting a second command signal containing information about said manual command to the slave robot assembly to actuate said slave surgical instrument;

wherein said master controller assembly detects the manual command and comprises at least one portable hand-held master input tool, to be hand-held and manipulated by a surgeon from various locations of an operating arena during surgery; said at least one portable hand-held master input tool being adapted to receive said manual command;

said master controller assembly is operatively connected to said slave robot assembly;

said at least one portable hand-held master input tool comprises a master tool body;

said master tool body defines a tool longitudinal axis, substantially coincident to an axis of longitudinal development of said master tool body, a tool radial direction, orthogonal to the tool longitudinal axis, and a tool circumferential direction, orthogonal to both the tool longitudinal axis and the tool radial direction;

said master tool body comprises a manipulandum surface, designed to be hand-held by surgeon's fingers;

said at least one portable hand-held master input tool is mechanically unconstrained from said slave robot assembly, said master tool body being movable, rotatable and spinnable by the surgeon;

said manipulandum surface is a convex surface, so that said master tool body-is rollable between the surgeon's fingers around the tool longitudinal axis;

said at least one portable hand-held master input tool further comprises a grip command detector device detecting said manual command, said manual command being directed to actuate the grip degree-of-freedom of motion of said at least one slave surgical grip device;

said grip command detector device comprises an operative portion surrounding the tool longitudinal axis;

said operative portion comprises at least one operative surface facing opposite to the tool longitudinal axis and for facing the surgeon's fingers, said operative portion being operable by said manual command, said manual command being a radially directed pressure action exerted at any point of the operative surface;

said master controller assembly further comprises a sensing assembly detecting said radially directed pressure action, so that said radially directed pressure action exerted at any point of said at least one operative surface determines a paired slave grip motion action of said at least one slave surgical grip device, so that said paired slave grip motion of said at least one slave surgical grip device lies in said predefined slave grip plane;

wherein said master tool body comprises a first body portion and a second body portion, said first body portion and said second body portion being movable with respect to each other, wherein said grip command detector device cooperates with said first body portion and said second body portion so that said radially directed pressure action exerted at any point of said at least one operative surface determines a relative motion of said first body portion and said second body portion along a predefined axis of movement;
wherein said predefined axis of movement is the tool longitudinal axis.

2. The master controller assembly according to claim 1, wherein said operative portion completely surrounds said tool longitudinal axis.

3. The master controller assembly according to claim 1, wherein said master tool body is extendable to modify a volume of said at least one portable hand-held master input tool in operative conditions.

4. The master controller assembly according to claim 1, wherein said sensing assembly detects relative motion of said first body portion and said second body portion along a predefined axis of movement.

5. The master controller assembly according to claim 1, wherein said relative motion of said first body portion and said second body portion is directed to move said first body portion and said second body portion away from each other.

6. The master controller assembly according to claim 1, wherein at least one of said first body portion and said second body portion comprises a guiding device guiding relative motion of said first body portion and said second body portion.

7. The master controller assembly according to claim 1, wherein:
said sensing assembly comprises a first sensor; and
said sensing assembly comprises a second sensor.

8. The master controller assembly according to claim 7, wherein said first sensor is integral with said first body portion of said master tool body; and wherein said second sensor is integral with said second body portion of said master tool body.

9. The master controller assembly according to claim 8, wherein said first body portion delimits a first slot receiving at least one portion of said sensing assembly;
wherein said first slot receives said first sensor;
wherein said sensing assembly comprises a second sensor; and
wherein said second slot receives said second sensor.

10. The master controller assembly according to claim 9, wherein said first slot faces opposite with respect to said second slot, so that a single arrangement of said sensing assembly is allowed; and
wherein said first slot is opposite to said second slot with respect to said tool longitudinal axis.

11. The master controller assembly according to claim 1, wherein said sensing assembly comprises a sterile sensor container, enclosing at least one of said a first sensor and a second sensor.

12. The master controller assembly according to claim 1, wherein:
said at least one operative surface is a discontinuous surface;
said at least one operative surface is a discontinuous surface in the tool circumferential direction; and
said operative portion comprises a plurality of strip elements arranged substantially oriented in the longitudinal direction, said plurality of strip elements extending longitudinally between a first connecting portion and a second connecting portion of the operative portion, defining longitudinal holes therebetween.

13. The master controller assembly according to claim 12, wherein said manipulandum surface is located onto said operative portion of said grip command detector device.

14. The master controller assembly according to claim 1, wherein said grip command detector device of said at least one portable hand-held master input tool comprises an elastic element biasing said at least one operative surface away from the tool longitudinal axis;
wherein said operative portion comprises a first connecting portion connected to said first body portion of said master tool body, and a second connecting portion connected to said second body portion of said master tool body, so that said radially directed pressure action exerted at any point of said at least one operative surface loads said elastic element; and
wherein said elastic element biases said first body portion and said second body portion of said master tool body approaching one another.

15. The master controller assembly according to claim 1, wherein:
said first body portion comprises a distal tool body and a stem element,
said distal tool body receives a portion of said stem element, so that said distal tool body is integral with said stem element;
said stem element comprises a first abutment portion;
said second body portion of said master tool body comprises a hollow bobbin and a proximal tool body;
said hollow bobbin comprises a second abutment portion;
said hollow bobbin is fit onto said stem element, so that said first abutment portion of the stem element faces said second abutment portion of the hollow bobbin;
an elastic element is fit onto said stem element and interposed between said first abutment portion of the stem element and said second abutment portion of the hollow bobbin; and
said elastic element biases said first abutment portion of the stem element away from said second abutment portion of the hollow bobbin.

16. The master controller assembly according to claim 1, wherein:
said operative portion surrounds a prevailing angular portion of said tool longitudinal axis; and
said prevailing angular portion covers along the circumferential direction an angle greater than 180 degrees.

17. A robotic surgery system comprising:
a master controller assembly according to claim 1;
a slave robot assembly, comprising a slave surgical instrument designed to operate on a patient anatomy, said slave surgical instrument comprising at least one slave surgical grip device operable to provide said surgical instrument with a grip degree-of-freedom of motion lying in a predefined slave grip plane; and
a control unit, for receiving a first command signal containing information about a manual command and for transmitting a second command signal containing information about said manual command to the slave robot assembly to actuate said slave surgical instrument;
wherein paired grip motion of said at least one slave surgical grip device lies in said predefined slave grip plane.

18. The robotic surgery system according to claim 17, further comprising at least one field generator generating a predefined field volume;
wherein said field generator is a magnetic field generator.

19. The robotic surgery system according to claim 17, wherein said at least one portable hand-held master input tool comprises a sensing assembly detecting position of said at least one portable hand-held master input tool within a predefined field volume.

20. A method for controlling a slave grip degree of freedom in a robotic surgery system, said robotic surgery system comprising:
- a master controller assembly, for detecting a manual command, the master controller assembly comprising a master input tool;
- a slave robot assembly, comprising a slave surgical instrument, designed to operate on a patient anatomy, said slave surgical instrument comprising at least one slave surgical grip device operable to provide a grip degree-of-freedom of motion lying in a predefined slave grip plane;
- a control unit, for receiving information on said manual command and for transmitting a command signal to the slave robot assembly said surgical instrument;

wherein:
- said master input tool comprises a master tool body, defining a volume of said master input tool;
- said master tool body defines a tool longitudinal axis, substantially coincident to an axis of longitudinal development of said master tool body, a tool radial direction, orthogonal to the tool longitudinal axis, and a circumferential direction, orthogonal to both the tool longitudinal axis and the tool radial direction;

the method comprising the following steps:
—A— applying a radial directed pressure action exerted at any point of an operative surface of said master input tool; and
—B— determining a paired slave grip motion action of said at least one surgical slave grip device, wherein said paired slave grip motion of said at least one slave surgical grip device lies in said predefined slave grip plane:
- wherein said master tool body comprises a first body portion and a second body portion, said first body portion and said second body portion being movable with respect to each other, and wherein the method comprises detecting a relative motion of said first body portion and said second body portion along a predefined axis of movement, and
- wherein the predefined axis of movement is the tool longitudinal axis of the master tool body.

* * * * *